US011540936B2

(12) United States Patent
Madden et al.

(10) Patent No.: US 11,540,936 B2
(45) Date of Patent: Jan. 3, 2023

(54) CARPOMETACARPAL THUMB BRACE

(71) Applicant: DJO, LLC, Vista, CA (US)

(72) Inventors: David Madden, Forest Lake, MN (US); Matthew Cozad, Edina, MN (US); Richard Gildersleeve, Carlsbad, CA (US)

(73) Assignee: DJO, LLC, Carlsbad, CA (US)

( * ) Notice: Subject to any disclaimer, the term of this patent is extended or adjusted under 35 U.S.C. 154(b) by 694 days.

(21) Appl. No.: 16/477,042

(22) PCT Filed: Jan. 19, 2018

(86) PCT No.: PCT/US2018/014441
§ 371 (c)(1),
(2) Date: Jul. 10, 2019

(87) PCT Pub. No.: WO2018/136748
PCT Pub. Date: Jul. 26, 2018

(65) Prior Publication Data
US 2019/0336317 A1  Nov. 7, 2019

Related U.S. Application Data

(60) Provisional application No. 62/449,221, filed on Jan. 23, 2017.

(51) Int. Cl.
*A61F 5/058* (2006.01)
*A61F 5/37* (2006.01)
*A61F 5/01* (2006.01)

(52) U.S. Cl.
CPC ............ *A61F 5/05866* (2013.01); *A61F 5/37* (2013.01); *A61F 2005/0186* (2013.01)

(58) Field of Classification Search
CPC ................... A61F 5/05866; A61F 5/37; A61F 2005/0186; A61F 5/0118; A61F 5/01
See application file for complete search history.

(56) References Cited

U.S. PATENT DOCUMENTS 5,713,837 A   2/1998  Grim et al.
5,771,901 A   6/1998  O'Brien
(Continued)

FOREIGN PATENT DOCUMENTS

WO   WO 14/148906   9/2014
WO   WO 15/028734   3/2015
(Continued)

OTHER PUBLICATIONS

International Search Report and Written Opinion dated May 15, 2018 in application No. PCT/US18/14441.

*Primary Examiner* — Tarla R Patel
(74) *Attorney, Agent, or Firm* — Knobbe, Martens, Olson & Bear LLP

(57) ABSTRACT

A brace for a carpometacarpal joint of a thumb includes a body made of an elastomeric material. The body includes a wrist strap configured to surround a wrist, a dorsal projection extending from the wrist strap, a first palmar strap extending between a proximal end connected to the wrist strap and a distal end configured to removably attach to the dorsal projection, and a second palmar strap extending between a proximal end connected to the wrist strap and a distal end configured to removably attach to the dorsal projection. The brace also includes a heat-moldable insert positioned within the body. The heat-moldable insert is configured so as to be positioned over a CMC joint of the thumb.

20 Claims, 10 Drawing Sheets

(56) References Cited

U.S. PATENT DOCUMENTS

| | | | |
|---|---|---|---|
| 5,787,896 A | | 8/1998 | Sackett |
| 5,899,870 A | * | 5/1999 | Deirmendjian ....... A61F 13/104 |
| | | | 128/880 |
| 5,921,945 A | * | 7/1999 | Gray ................... A61F 5/05866 |
| | | | 602/5 |
| 6,196,985 B1 | * | 3/2001 | Slautterback ....... A61F 5/05866 |
| | | | 128/880 |
| 6,261,252 B1 | | 7/2001 | Darcey |
| 7,056,298 B1 | * | 6/2006 | Weber ................... A61F 5/0118 |
| | | | 2/21 |
| 7,713,223 B2 | | 5/2010 | Weber |
| 7,854,714 B1 | | 12/2010 | Weber et al. |
| 7,887,497 B2 | | 2/2011 | Weber et al. |
| 8,066,655 B2 | | 11/2011 | Prather |
| 2006/0149180 A1 | | 7/2006 | Phelen |
| 2006/0264792 A1 | * | 11/2006 | Bonn ................... A61F 5/0118 |
| | | | 602/21 |
| 2008/0262400 A1 | | 10/2008 | Clark et al. |
| 2012/0310130 A1 | * | 12/2012 | Crompton ............. A61F 5/0118 |
| | | | 602/21 |
| 2013/0197411 A1 | | 8/2013 | Bella |
| 2013/0253400 A1 | | 9/2013 | Massa |
| 2015/0157483 A1 | | 6/2015 | Grunden et al. |
| 2016/0206464 A1 | | 7/2016 | Grange |

FOREIGN PATENT DOCUMENTS

| | | |
|---|---|---|
| WO | WO 15/055304 | 4/2015 |
| WO | WO 16/027090 | 2/2016 |

* cited by examiner

CARPOMETACARPAL THUMB BRACE

PRIORITY APPLICATIONS

This application is a U.S. National Phase Application of International Application No. PCT/US2018/014441, filed Jan. 19, 2018, which claims priority to U.S. Provisional Application No. 62/449,221, filed Jan. 23, 2017, each of which is incorporated herein by reference. Any and all applications for which a foreign or domestic priority claim is identified in the Application Data Sheet as filed with the present application are hereby incorporated by reference under 37 CFR 1.57.

BACKGROUND

Field

This disclosure relates to orthopedic braces. In particular, a carpometacarpal thumb brace is disclosed.

Description

The carpometacarpal ("CMC") joint of the thumb (also referred to as the basal joint of the thumb, the first carpometacarpal joint, or the trapeziometacarpal joint) is formed between the metacarpal bone of the thumb and the trapezium bone of the wrist. The CMC joint permits a wide range of motion for the thumb.

Unfortunately, arthritis of the CMC joint is common. Arthritis can cause the CMC joint to become inflamed and can make movement of the thumb painful. In early stages, arthritic pain may occur only with motion of the CMC joint. In later stages, pain may be present even at rest. In addition to pain, sufferers of arthritis of the CMC joint often have difficulty using the thumb, for example, to grip objects.

SUMMARY

In one aspect, a brace for a carpometacarpal joint of a thumb is disclosed. The brace includes a body made of an elastomeric material. The body includes a wrist strap configured to surround a wrist, a dorsal projection extending from the wrist strap, the dorsal projection configured to extend across a portion of a dorsum of a hand, a first palmar strap extending between a proximal end connected to the wrist strap and a distal end, the first palmar strap configured to extend across a portion of a palm of the hand and over a purlicue of the hand, the distal end configured to removably attach to the dorsal projection, and a second palmar strap extending between a proximal end connected to the wrist strap and a distal end, the second palmar strap configured to extend across a portion of the palm of the hand and over the purlicue of the hand, the distal end configured to removably attach to the dorsal projection. The brace also includes an insert positioned within the body. The insert comprises a heat-moldable material that is pliable above a temperature and substantially stiff below the temperature, the insert positioned within the body to be positioned over a carpometacarpal joint of a thumb. In some embodiments, the elastomeric material comprises silicone. In some embodiments, the elastomeric material comprises a thermoplastic elastomer. In some embodiments, the temperature that affects the pliability (or stiffness) of the heat-moldable material is between approximately 130° F. and approximately 250° F.

In another aspect, a brace for a carpometacarpal joint of a thumb is disclosed. The brace includes a body having a wrist strap, a dorsal projection extending from the wrist strap, a first palmar strap extending between a proximal end connected to the wrist strap and a distal end configured to removably attach to the dorsal projection, and a second palmar strap extending between a proximal end connected to the wrist strap and a distal end configured to removably attach to the dorsal projection.

In some embodiments, the body comprises an elastomeric material. In some embodiments, the elastomeric material comprises silicone. In some embodiments, the elastomeric material comprises a thermoplastic elastomer. In some embodiments, the brace further comprises an insert embedded within the body to be positioned over a CMC joint of the thumb when the brace is worn. In some embodiments, the insert comprises a stiff material. In some embodiments, the insert comprises a heat-moldable material that is pliable above a temperature and stiff below the temperature. In some embodiments, the temperature is between approximately 130° F. and approximately 250° F. In some embodiments, the wrist strap is configured in size and shape to encircle a patient's wrist when the brace is worn. In some embodiments, the first and second palmar straps are each configured in size and shape to extend across a portion of a palm of the hand and over a purlicue of the hand. In some embodiments, the dorsal projection is configured in size and shape to extend across a portion of a dorsum of the hand.

In another aspect, a brace for a carpometacarpal joint of a thumb is disclosed. The brace includes a body having a wrist strap configured to encircle a patient's wrist when the brace is worn, and a strap connected on a first end to a first location of the wrist strap and connected on a second end to a second location of the wrist strap. The strap is configured in size and shape to extend across a portion of the patient's palm, over the purlicue, and across a portion of the dorsum of the patient's hand. The brace also includes an insert comprising a heat-moldable material that is pliable above a temperature and stiff below the temperature.

In some embodiments, the temperature is between approximately 130° F. and approximately 250° F. In some embodiments, the body comprises an elastomeric material. In some embodiments, the elastomeric material comprises silicone. In some embodiments, the strap comprises a dorsal projection extending from the first location of the wrist strap, and a palmar strap extending between a proximal end connected to the second location wrist strap and a distal end configured to removably attach to the dorsal projection. In some embodiments, the dorsal projection is configured in size and shape to extend over a portion of the dorsum of the hand when the brace is worn. In some embodiments, the palmar strap is configured is size and shape to extend across a portion of the palm and over the purlicue of the hand when the brace is worn.

BRIEF DESCRIPTION OF THE DRAWINGS

The features and advantages of the CMC braces and methods described herein will become more fully apparent from the following description and appended claims, taken in conjunction with the accompanying drawings. These drawings depict only several embodiments in accordance with the disclosure and are not to be considered limiting of its scope. In the drawings, similar reference numbers or symbols typically identify similar components, unless context dictates otherwise. In some instances, the drawings may not be drawn to scale.

DETAILED DESCRIPTION

The following detailed description describes embodiments of CMC thumb braces and methods, some of which are illustrated in the figures. These embodiments are not intended to be limiting, and various modifications, variations, combinations, etc., of the features of these embodiments are possible and within the scope of this disclosure.

In some embodiments, the CMC thumb braces described herein provide stabilization, support, splinting, bracing, compression, and/or pain relief for the CMC thumb joint. The CMC thumb braces may be used to treat and/or prevent arthritis of the CMC joint. The CMC thumb braces may alleviate pain associated with arthritis of the CMC joint. In some embodiments, the CMC thumb braces are configured to abduct the thumb and/or seat the CMC joint. In some embodiments, the CMC thumb braces provide stabilization, support, splinting, and/or bracing for the CMC thumb joint while still permitting movement of the thumb. That is, in some embodiments, the CMC thumb braces are non-immobilizing. In some embodiments, the CMC thumb braces partially limit motion of the thumb.

In some embodiments, the CMC thumb braces include one or more adjustable tension mechanisms that are configured to provide variable and/or changeable support. For example, in some embodiments the CMC thumb brace may include one or more fasteners that may secure to various locations of the brace to attach a strap that secures the brace to the patient's thumb/hand. The fasteners can be attached to different locations to provide various levels of tension, support, and/or immobilization.

In some embodiments, the CMC thumb braces are configured to be patient specific. For example, in some embodiments, the CMC thumb braces (or at least a portion thereof) can be custom fit or custom molded to conform to a particular patient's anatomy. For example, at least a portion of the CMC thumb braces can be heat-moldable. In some embodiments, the heat-moldable portion can be an insert. In some embodiments, the CMC thumb braces can have a low profile and/or be water resistant or water proof.

Figure 1:
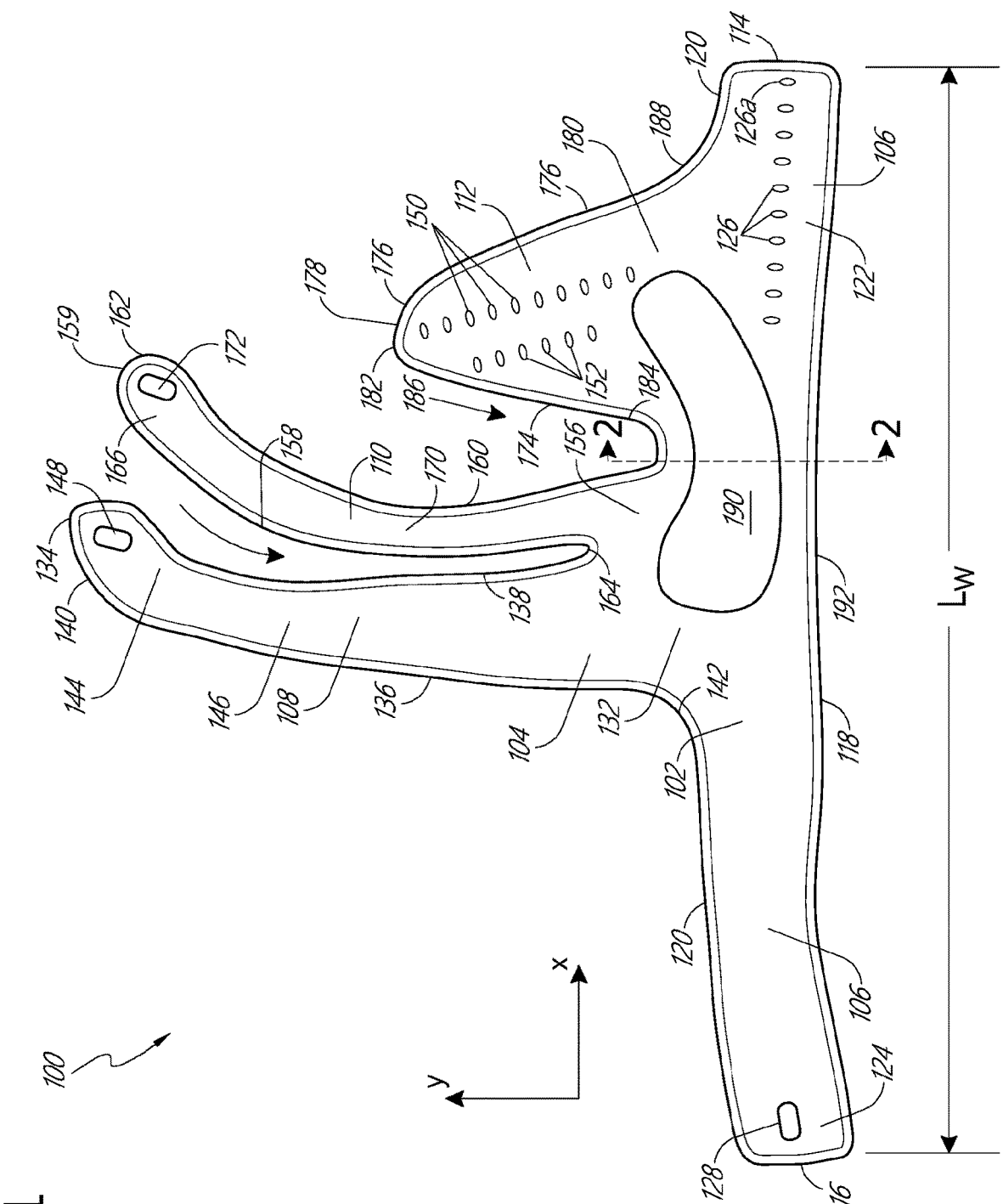
FIG. 1 is a plan view of an exterior side of an embodiment of a CMC thumb brace, illustrated when not worn by a patient and lying flat.

FIG. 1 is a plan view of an exterior side 104 of one embodiment of a CMC thumb brace 100 (referred to herein as the "brace 100"), illustrated when not worn by a patient and lying flat. The brace 100 is illustrated when worn by a patient, according to an embodiment, in FIGS. 6-8. The exterior side 104 can be the side of the brace 100 that faces away from a patient when the brace 100 is worn. An interior side of the brace 100 may contact the patient when the brace 100 is worn. The interior side is opposite the exterior side 104.

The brace 100 includes a body 102. In the illustrated embodiment, the body 102 includes a wrist strap 106, a first palmar strap 108, a second palmar strap 110, and a dorsal projection 112. In some embodiments, the body 102 is made from one or more elastomeric materials. In some embodiments, the elastomeric materials include a thermoplastic elastomer (TPE) or thermoplastic rubber that exhibits both thermoplastic and elastomeric properties. In some embodiments, the elastomeric materials comprise silicone. In some embodiments, the elastomeric materials are stretchable, exhibit low fatigue, are abrasion and chemical resistant, and/or are soft. In some embodiments, the one or more elastomeric materials allow the body 102 to be expandable, recoverable, and/or flexible. As used herein, "elastomeric material" refers to a material that is capable of being easily expanded (in other words, stretched) or compressed and that resumes or recovers its former shape (in other words, its pre-stretch or pre-compression shape) once released. Something that has the ability to resume its former shape after expansion or compression is referred to herein as being "recoverable." Something that is expandable and recoverable may also be referred to herein as being "elastically stretchable."

In some embodiments, the body 102 is flexible and is capable of conforming to the general area of the body to be supported without substantial stretching; however, it is contemplated that the body 102 of the brace 100 may need to be stretched in order to conform to the general area of the body part to be supported. In some embodiments, the body 102 may be stretched over the body part to which it is applied so as to provide a degree of compression to the body part. As used herein, "flexible" generally refers to the ability (e.g., of a material or an article) to bend freely and repeatedly without breaking and/or to conform to the shape of the body part to which the flexible material (or article) is applied.

In some embodiments, the body 102 is formed from a transparent or translucent material. This may allow for visual inspection of areas covered by the body 102 of the brace 100.

Figure 11:
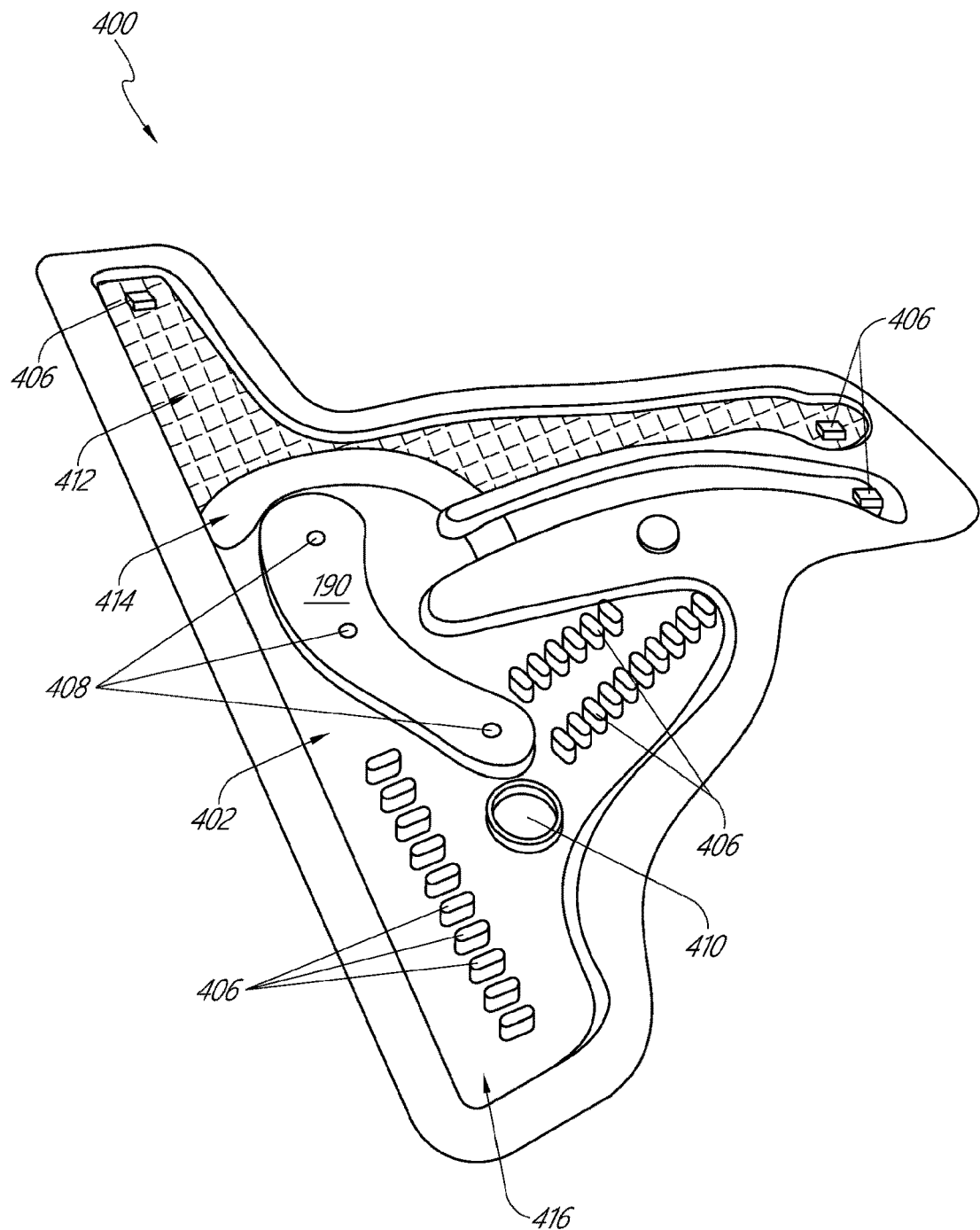
FIG. 11 illustrates a perspective view of an embodiment of a mold that can be used to manufacture a CMC thumb brace.

In some embodiments, the brace 100 and the body 102 can be molded, for example, using the mold 400 shown in FIG. 11. For example, the mold 400 may include a depression 402 shaped to form the body 102. An elastomeric material in liquid form can be poured into the mold 400 and allowed to solidify (in some embodiments, into a solid that is expandable, recoverable, and/or flexible) to form the body 102. Other methods for manufacturing the brace 100 and the body 102 are possible.

The wrist strap 106 extends generally in a first direction between a first edge 114 and a second edge 116. For example, as illustrated in FIG. 1, the wrist strap 106 extends generally in the x-direction (relative to the illustration) between the first edge 114 and the second edge 116. Between the first edge 114 and the second edge 116, the wrist strap 106 is partially defined by a proximal edge 118 and a distal edge 120. Each of the proximal edge 118 and the distal edge 120 extend generally in the first-direction (for example, the x-direction). In general, a length L of the wrist strap 106, measured between the first edge 114 and the second edge 116, is configured to be sufficient to extend around and partially overlap a patient's wrist. For example, in various embodiments, the length L may be between approximately 4 inches and approximately 12 inches, although other lengths are also possible.

Figure 6:
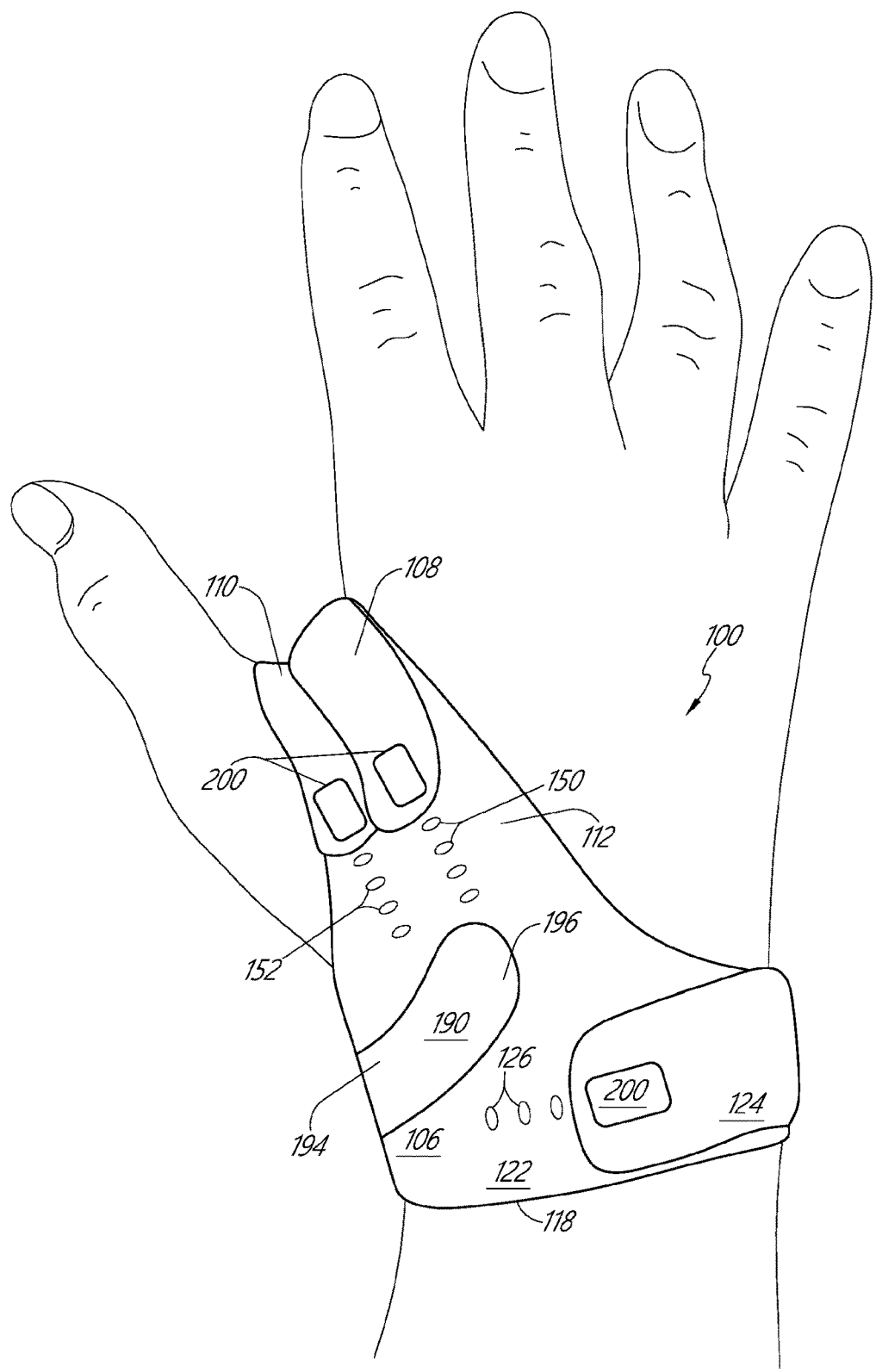
FIG. 6 is a dorsal view of a right hand wearing the CMC thumb brace of FIG. 1.
Figure 7:
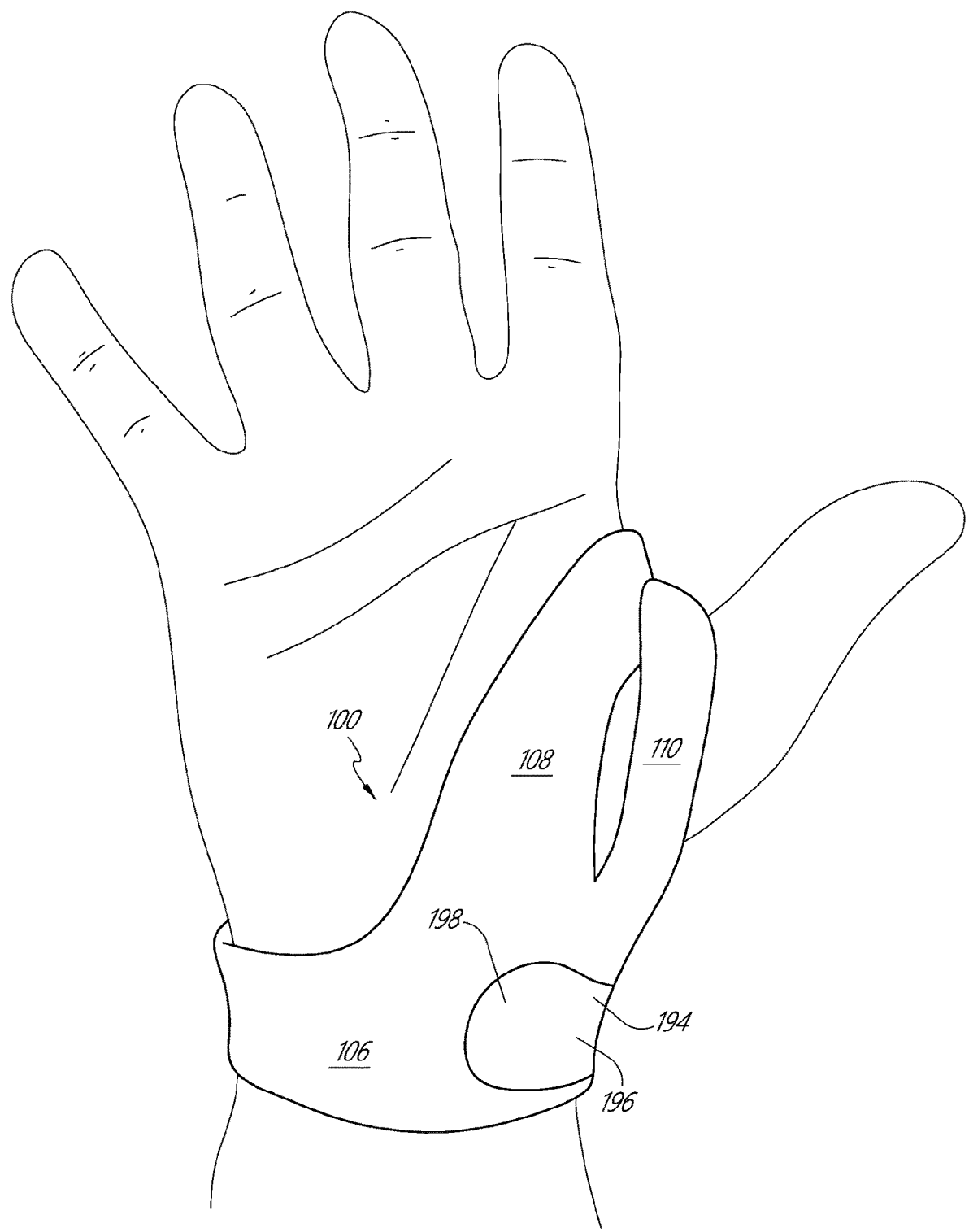
FIG. 7 is palmar view of a right hand wearing the CMC thumb brace of FIG. 1.
Figure 8:
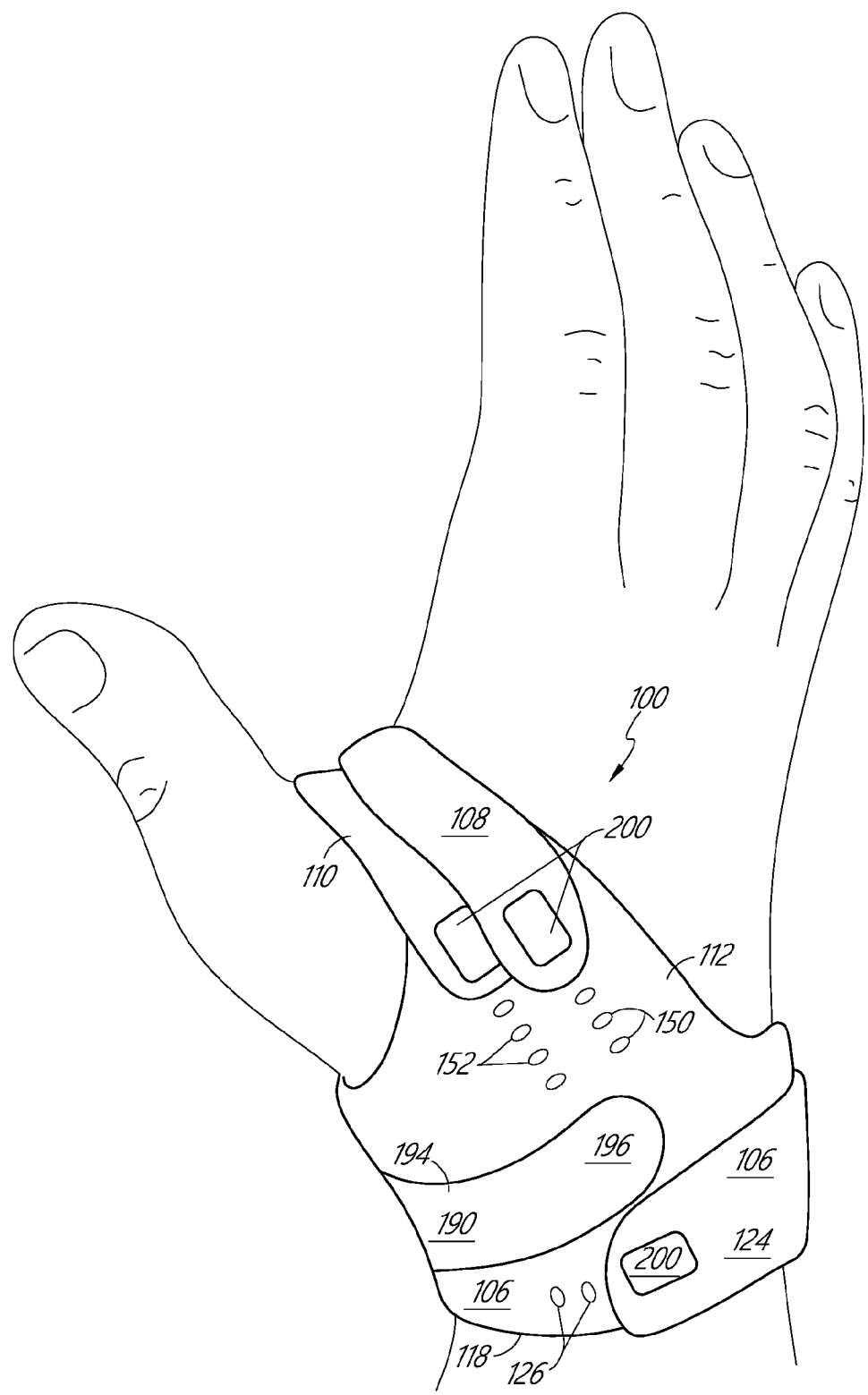
FIG. 8 is a perspective view of a right hand wearing the CMC thumb brace of FIG. 1.

The wrist strap 106 is configured to be secured around the patient's wrist when the brace 100 is worn (see FIGS. 6-8, for example). In some embodiments, the wrist strap 106 includes a closure system for securing a second end 124 of the wrist strap 106 to a first end 122 of the wrist strap 106, such that the wrist strap 106 forms a closed band-shape that surrounds the patient's wrist. In some embodiments, when secured around the patient's wrist, the second edge 116 overlaps the first edge 114, or vice versa.

In the illustrated embodiment, the closure system of the wrist strap 106 includes a plurality of apertures 126 extending through the first end of the wrist strap 106. The plurality of apertures 126 can be aligned along an axis. For example, in the illustrated embodiment, the plurality of apertures 126 are aligned along an axis that extends in the x-direction. In the illustrated embodiment, ten apertures 126 are shown, although other numbers of apertures (fewer and greater) are possible. In the illustrated embodiment, spacing between apertures 126 is even, although this need not be the case in all embodiments. In the illustrated embodiment, a first 126a of the apertures 126 is positioned near the first edge 114 and each successive aperture 126 is positioned inwardly (i.e., toward the second edge 116) from the first 126a of the apertures 126. The illustrated embodiment also includes an aperture 128 extending through the second end 124 of the wrist strap 106. The aperture 126 can be positioned near the second edge 116. The aperture 128 is configured to receive a fastener or connector therein (see, for example, fastener 200 of FIGS. 4-5). The fastener or connector is configured to secure the second end 124 to the first end 122 of the wrist strap 106. For example, in some embodiments, the fastener extends through both the aperture 126 of the second end 124 and one or more of the apertures 126 of the first end 122. In some embodiments the apertures 126 and the aperture 128 can be reversed. That is the aperture 128 can be positioned in proximity to the first edge 114 and the apertures 126 can be positioned in proximity to the second edge 116.

Figure 4:
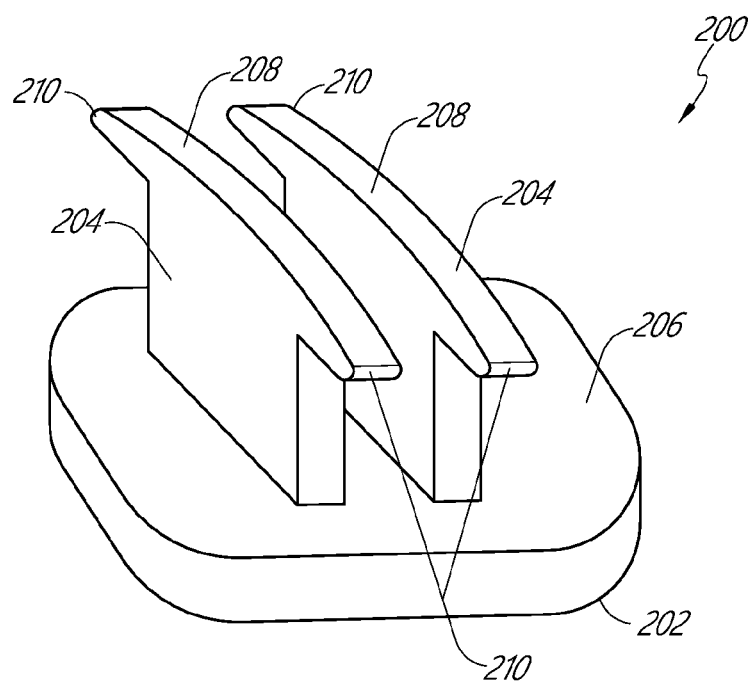
FIG. 4 is a perspective view of an embodiment of a fastener that can be used with the CMC thumb brace of FIG. 1.

FIG. 4 is a perspective view of an example connector or fastener 200 that can be used with the brace 100. In the illustrated embodiment, the fastener 200 includes a base 202 and two projections 204. The projections 204 extend perpendicularly away from a surface 206 of the base 202. A distal end 208 (that is, the free end of the projection 204 opposite the connection to the base 202) of each projection 204 includes prongs 210 that extend outwardly from the projection 204. Thus, in some embodiments, each protrusion 204 is substantially T-shaped. Other embodiments of the fastener are possible. For example, the fastener may include a single projection. Alternatively, the fastener 200 can comprise a snap, button, clasp, etc.

With reference again to FIG. 1, the fastener 200 can be inserted through the aperture 128 of the second end 124 such that the projections 204 extend through the aperture 128 and the surface 206 of the base 202 of the fastener 200 may be brought into contact with the exterior surface 104 of the body 102. To secure the second end 124 to the first end 122, the projections 204 can then be inserted through two of the plurality of apertures 126 of the first end 122, with each projection 204 being inserted through one of the plurality of apertures 126. The prongs 210 then secure the fastener 200 in place.

Figure 5:
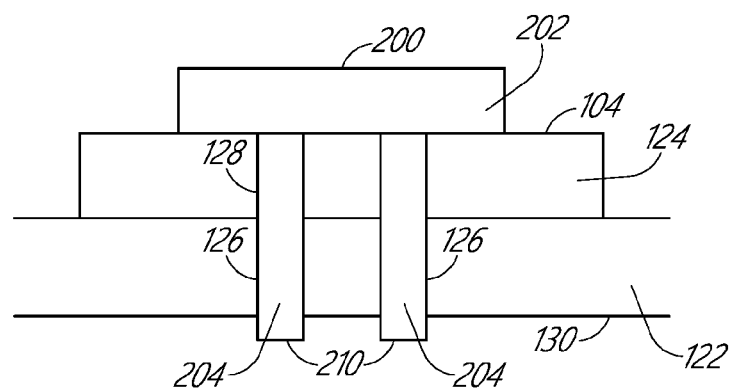
FIG. 5 is a cross-sectional view of the fastener of FIG. 4, illustrated in use.

FIG. 5 is a cross-sectional view of the fastener 200 in use securing the second end 124 to the first end 122, according to one embodiment. As shown, the second end 124 can be positioned on top of the first end 122 such that the aperture 128 is aligned with two of the plurality of apertures 126. The fastener 200 can then be inserted through the aperture 128 and the two of the plurality of apertures 126. One of the projections 204 can extend through the aperture 128 and one of the apertures 126. The other projection 204 can extend through the aperture 128 and the other of the apertures 126. The surface 206 of the base 202 can be positioned on the exterior surface 104 of the second end 124. The prongs 210 can be positioned on an interior side 130 of the first end 122. The prongs 210 may prevent the fastener 200 from being inadvertently pulled back through the apertures 126, 128. Although one particular configuration is illustrated in FIG. 5, other configurations are possible. For example, the first end 122 can be positioned on top of the second end 124 and/or the fastener 200 can be inserted from the opposite direction (that is, such that the base 202 is located on the interior side 130 and the prongs 210 are located on the exterior side 104).

Returning again to FIG. 1, the plurality of apertures 126 can allow the brace 100 to be used on patients with wrists of different sizes. For example, by inserting the fastener 200 through apertures 126 nearer the first edge 114, the brace 100 can be used with larger wrists and by inserting the fastener 200 through apertures 126 nearer the second edge 116 the brace 100 can be used with smaller wrists. Similarly, the plurality of apertures 126 can allow a user to adjust the fit and/or tightness of the brace 100 around the wrist. For example, by inserting the fastener 200 through apertures 126 nearer the first edge 114, the brace 100 can provide a looser fit and by inserting the fastener 200 through apertures 126 nearer the second edge 116 the brace 100 can provide a tighter fit. Examples of the wrist strap 106 secured around a patient's wrist by the fastener 200 are shown in FIGS. 6-8. Additionally or alternatively, the brace 100 can be provided in a plurality of different sizes (e.g., small, medium, large, etc.) to accommodate wrists of different sizes.

In some embodiments, other closure systems for securing the wrist strap 106 around the patient's wrist can be implemented. For example, the brace 100 can include snaps, buckles (e.g., similar to a wrist watch), or hook and loop material to secure the brace 100. In some embodiments, the wrist strap 106 is configured as a continuous loop, such that no fastener is needed. For example, the wrist strap 106 can be configured as a continuous loop of elastic material that can be stretched to pass over the user's hand and which can then tighten (recover) around the wrist.

The first palmar strap 108, the second palmar strap 110, and the dorsal projection 112 may each extend generally away from the distal edge 120 of the wrist strap 106 in a second direction that is perpendicular to the first direction. For example, as illustrated in FIG. 1, each of the first palmar strap 108, the second palmar strap 110, and the dorsal projection 112 extend generally away from the distal edge 120 of the wrist strap 106 in the y-direction.

The first palmar strap 108 and the second palmar strap 110 are each referred to as "palmar" because, in some embodiments, when the brace 100 is worn by the patient, the first and second palmar straps 108, 110 extend at least partially over a palm (or inside surface) of the hand (see FIGS. 6-8, for example). The dorsal projection 112 is referred to as "dorsal" because, in some embodiments, when the brace 100 is worn by the patient, the dorsal projection extends at least partially over a dorsum (or outside surface) of the hand (again, see FIGS. 6-8, for example). As illustrated in FIG. 1, the second palmar strap 110 is connected to the wrist strap 106 between the connection of the first palmar strap 108 to the wrist strap 106 and the dorsal projection 112. In the illustrated implementation, the first palmar strap 108 and the second palmar strap 110 extend from the wrist strap 106 to a length that is longer than a length that the dorsal projection 112 extends from the wrist strap 106. Also, in the illustrated implementation, the distal end 134 of the first palmar strap 108 extends from the wrist strap 108 farther than a distal end 159 of the second palmar strap 110 extends from the wrist strap 108. In the example shown in FIG. 1, the first palmar strap 108 is separated from the second palmar strap 110 by a gap that is smaller than a gap separating the second palmar strap 110 and the dorsal projection 112.

Still referring to FIG. 1, in the illustrated embodiment, the first palmar strap 108 extends between a proximal end 132 and a distal tip 134. The proximal end 132 may be connected to or extend from the distal edge 120 of the wrist strap 106. The palmar strap 108 may include a first edge 136, a second edge 138, and a distal edge 140. In some embodiments, the first edge 136 and the second edge 138 are substantially parallel, extending generally in the y-direction. In some embodiments, the distance between the first edge 136 and the second edge 138 narrows along the first palmar strap 108 moving from the wrist strap 106 to the distal tip 134. In some embodiments, the first edge 136 and the second edge 138 are substantially straight. In some embodiments, the first edge 136 and the second edge 138 may include one or more curves. In some embodiments, the first edge 136 is continuous with a portion of the distal edge 120 of the wrist strap 106. The first edge 136 and the distal edge 120 may meet at an intersection 142. In some embodiments, the intersection 142 may include a curve between the first edge 130 and the distal edge 120.

At a distal end 144, the first edge 136 and the second edge 138 are connected by the distal edge 140 of the first palmar strap 108. The distal edge 140 may include a curve connecting the edge 136 and the second edge 138. The curve of the distal edge 140 may define a lobe shape at the distal end 144 of the first palmar strap 108. The distal end 144 may be curved or bent with respect to a main portion 146 (in other words, the portion between the first edge 136 and the second edge 138) of the first palmar strap 108. In some embodiments, the distal end 144 curves in a direction toward the second palmar strap 110 and/or the dorsal projection 112. In some embodiments, the main portion 146 may also curve toward the second palmar strap 110 and/or the dorsal projection 112. In some embodiments, the first palmar strap 108 may comprise a finger-like shape.

In the illustrated embodiment, the first palmar strap 108 includes an aperture 148 in the distal end 144. The aperture 148 may be configured in size and shape to receive a fastener 200 to connect the distal end 144 of the first palmar strap 108 to one or more of a plurality of apertures 150, 152 on the dorsal projection (as shown, for example, in FIGS. 6-8). In some embodiments, when the brace 100 is worn, the first palmar strap 108 extends from the wrist strap 106, across a portion of a palm of a hand, over the purlicue of the hand (the space or webbing connecting the thumb and index finger) and connects to the dorsal projection 112. The connection between the first palmar strap 108 and the dorsal projection 112 can be made using the fastener 200 in a manner substantially similar to the connection between the second end 124 and the first end 122 of the wrist strap 106 described above (see, for example, FIGS. 4 and 5). In some embodiments, other closure systems for connecting the first palmar strap 108 to the dorsal projection 112 can be implemented. For example, the brace 100 can include snaps, buckles (e.g., similar to a wrist watch), or hook and loop material for connecting the first palmar strap 108 to the dorsal projection 112.

In some embodiments, the second palmar strap 110 is positioned substantially adjacent to the first palmar strap 110 in a direction toward the dorsal projection 112. In some embodiments, a space 154 is formed between the first palmar strap 108 and the second palmar strap 110. In some embodiments, a width of the space 154 increases in a direction moving away from the wrist strap 106.

The second palmar strap 110 extends between a proximal end 156 and a distal tip 159. The proximal end 156 may be connected to or extend from the wrist strap 106. In the illustrated embodiment, a portion of the proximal end of the second palmar strap 110 is also connected to a portion of the proximal end 132 of the first palmar strap 108. The second palmar strap 110 may include a first edge 158, a second edge 160, and a distal edge 162. In the illustrated embodiment, the first edge 158 and the second edge 160 are generally parallel, extending generally in the y-direction and curving toward the dorsal projection 112. In some embodiments, the distance between the first edge 158 and the second edge 160 narrows along the second palmar strap 110 moving from the wrist strap 106 toward the distal tip 159. In some embodiments, the distance between the first edge 158 and the second edge 160 widens along the second palmar strap 110 moving from the wrist strap 106 toward the distal tip 159. In some embodiments, the first edge 158 and the second edge 160 are substantially straight. In some embodiments, the first edge 158 and the second edge 160 may include one or more curves. In some embodiments, the first edge 158 is continuous with the second edge 138 of the first palmar strap 108. The first edge 158 of the second palmar strap 110 and the second edge 138 of the first palmar strap 108 may meet at an intersection 164. In some embodiments, the intersection 164 may include a curve between the first edge 158 and the second edge 138.

At a distal end 166, the first edge 158 and the second edge 160 are connected by the distal edge 162 of the second palmar strap 110. The distal edge 162 may include a curve connecting the first edge 158 and the second edge 160. The curve of the distal edge 162 may define a lobe shape at the distal end 166 of the second palmar strap 110. The distal end 166 may be curved or bent with respect to a main portion 170 (in other words, the portion between the first edge 158 and the second edge 160) of the second palmar strap 110. In some embodiments, the distal end 166 curves in a direction toward the dorsal projection 112. In some embodiments, the main portion 170 may also curve toward the dorsal projection 112. In some embodiments, the second palmar strap 110 may comprise a finger-like shape.

In the illustrated embodiment, the second palmar strap 110 includes an aperture 172 in the distal end 166. The aperture 172 may be configured in size and shape to receive a fastener 200 to connect the distal end 166 of the second palmar strap 110 to one or more of the plurality of apertures 150, 152 on the dorsal projection (as shown, for example, in FIGS. 6-8). In some embodiments, when the brace 100 is worn, the second palmar strap 110 extends from the wrist strap 106, across a portion of the palm of the hand, over the purlicue of the hand and connects to the dorsal projection 112. The connection between the second palmar strap 110 and the dorsal projection 112 can be made using the fastener 200 in a manner substantially similar to the connection between the second end 124 and the first end 122 of the wrist strap 106 described above (see, for example, FIGS. 4 and 5). In some embodiments, other closure systems for connecting the second palmar strap 110 to the dorsal projection 112 can be implemented. For example, the brace 100 can include snaps, buckles (e.g., similar to a wrist watch), or hook and loop material for connecting the second palmar strap 110 to the dorsal projection 112.

In the illustrated embodiment, the brace 100 includes two palmar straps (the first palmar strap 108 and the second palmar strap 110). In some embodiments, only one of these is included (for example, either the first palmar strap 108 or the second palmar strap 110) and the other is omitted. In some embodiments, the first palmar strap 108 and the second palmar strap 110 can be combined to form a single palmar strap. In some embodiments, more than two palmar straps (for example, three, four, or more) may be included.

As mentioned previously, the brace 100 can also include a dorsal projection 112, for example, as illustrated in FIG. 1. The dorsal projection 112 may extend from the wrist strap 106 from a proximal portion 180 to a distal tip 182. The proximal portion 180 can be connected to the wrist strap 106. In the illustrated embodiment, the dorsal projection 112 includes a first edge 174, a second edge 176, and a distal edge 178. The first edge 174 can be connected to the second edge 160 of the second palmar strap 110 at an intersection 184. The intersection 184 can include a curve. A space 186 is formed between the dorsal projection 112 and the second palmar strap 110. When the brace 100 is worn, the thumb may extend through the space 186 (see, for example, FIGS. 6-8). In some embodiments, a width of the space 186 increases in a direction moving away from the wrist strap 106. In some embodiments, the second edge 176 of the dorsal projection 112 is continuous with a portion of the distal edge 120 of the wrist strap 106. The second edge 176 and the distal edge 120 may meet at an intersection 188. In some embodiments, the intersection 188 may include a curve between the second edge 176 and the distal edge 120.

In the illustrated embodiment, a width of the dorsal projection 112 (measured between the first edge 174 and the second edge 176) narrows in a direction moving away from the wrist strap 106, such that the dorsal projection 112 has a substantially triangular shape. Other shapes for the dorsal projection 112 are also possible, as discussed below. The distal edge 178 connects the first edge 174 and the second edge 176. The distal edge 178 may be curved.

As mentioned above, the dorsal projection 112 may include a plurality of apertures 150 and a plurality of apertures 152. The apertures 150, 152 can be used to connect the first and second palmar straps 108, 110 to the dorsal projection 112. In the illustrated embodiment, the apertures 150 are arranged along an axis. Ten apertures 150 are illustrated, although other numbers (greater than fewer) are possible. In the illustrated embodiment, the apertures 152 are also arranged along an axis. Six apertures 152 are illustrated, although other numbers (greater and fewer) are possible. In some embodiments, the axes of the first and second apertures 150, 152 are substantially parallel. In some embodiments, the axes are straight. In some embodiments the axes are curved. In some embodiments, the axes of the first and second apertures 150, 152 are not parallel. In some embodiments, the axes of the first and second apertures 150, 152 extend generally in the y-direction. In some embodiments, the axes of the first and second apertures 150, 152 are angled with respect to the axis of the apertures 126. In some embodiments, the angle the axis of the first and/or second apertures 150, 152 with respect to the axis of the apertures 126 is about 90 degrees, about 85 degrees, about 80 degrees, about 75 degrees, about 70 degrees, about 65 degrees, or about 60 degrees, or smaller (as well as all ranges listed between the listed angles).

The apertures 150, 152 provide a plurality of connection points for the first and second palmar straps 108, 110 allowing for the fit and tightness of the brace 100 to be adjusted to fit the anatomy of a particular patient or to vary the amount of support or compression provided by the brace 100. In some embodiments, the first palmar strap 108 is connected to the apertures 150 and the second palmar strap 110 is connected to the apertures 152, such that the first and second palmar straps 108, 110 run generally parallel over the purlicue of the hand. In some embodiments, the first palmar strap 108 is connected to the apertures 152 and the second palmar strap 110 is connected to the apertures 150 such that the first and second palmar straps 108, 110 cross each other over the purlicue of the hand (either the first palmar strap 108 or the second palmar strap 110 may be on top). In some embodiments, the cross of the first and second palmar straps 108, 110 (if present) may occur over the dorsum or the palm of the hand.

In some embodiments, the dorsal projection 112 can be omitted and the first and second palmar strap 108, 110 can connect to the wrist strap 106. In some embodiments, more than one dorsal projection 112 can be included, with each dorsal projection 112 configured to connect to one of the first and second palmar straps 108, 110.

In some embodiments, a length of the palmar straps 108, 110 is longer than a length of the dorsal projection 112, such that when worn, the palmar straps 108, 110 extend over a portion of the palm, over the purlicue, and connect to the dorsal projection 112 over the dorsum of the hand. This need not be the case in all embodiments, however, and the lengths of the palmar straps 108, 110 and dorsal projection 112 can be varied such that the connections between the palmar straps 108, 110 and dorsal projection 112 can occur over the palm or purlicue. In some embodiments, the palmar straps 108, 110 and dorsal projection 112 are continuously formed such that no connection between the palmar straps 108, 110 and dorsal projection 112 is needed. That is, the palmar straps 108, 110 and dorsal projection 112 can form one or more continuous loops or straps extending from the wrist strap 106 configured to extend across the palm, over the purlicue, and across the dorsum.

Figure 2:
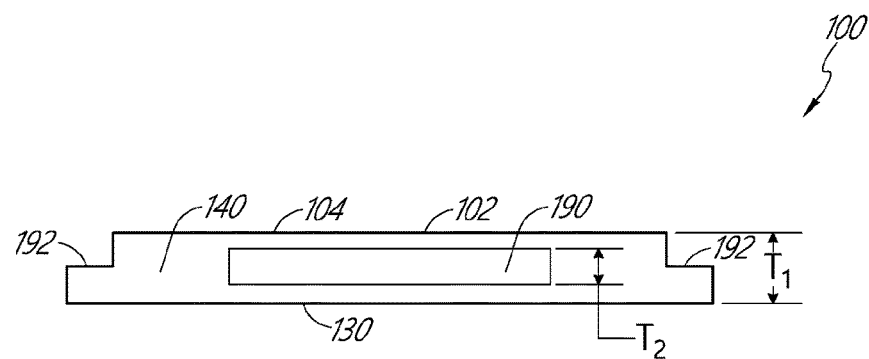
FIG. 2 is a cross-sectional view of the CMC thumb brace taken along the line shown in FIG. 1.

As shown in the cross-sectional view of FIG. 2, the brace 100 may have a thickness $T_1$ as shown. In some embodiments, the thickness $T_1$ is approximately 1 cm, 7.5 mm, 5 mm, 4 mm, 3 mm, 2 mm, or 1 mm. Other thicknesses are also possible. As shown in FIGS. 1 and 2, the body 102 may include a lip 192 formed around the edges of the body 102. The lip 192 may be formed as a region of reduced thickness. The lip 192 may be, in some embodiments, approximately one half the thickness $T_1$.

In the illustrated embodiment, the brace 100 also includes an insert 190. The insert 190 is shown in greater detail in FIG. 3. The insert 190 can be configured to provide additional support for the CMC joint. In some embodiments, the insert 190 can be positioned on (or in) the brace 100 so as to be positioned over the CMC joint when the brace 100 is worn. In some embodiments, the insert 190 can be positioned on (or in) the brace 100 so as to be positioned below the CMC joint (in other words, up the arm below the CMC joint) when the brace 100 is worn.

In some embodiments, the insert 190 is made of plastic or other similar materials. In some embodiments, the insert 190 is not elastic or recoverable. In some embodiments, the insert 190 is flexible so as to confirm to the shape of the patient's wrist. In some embodiments, the insert 190 is stiff or rigid. In some embodiments, the insert 190 is formed with a curved shape that wraps around the patient's wrist. As will be described below, in some embodiments, the insert 190 is made of a heat formable material. In some embodiments, the insert 190 can be omitted.

In some embodiments, the insert 190 is embedded within the body 102 of the brace 100. FIG. 2 is a cross-sectional view of the brace 100 taken along the line shown in FIG. 1. As shown in FIG. 2, the insert 190 is included within the body 102 between the exterior surface 104 and the interior surface 130. In some embodiments, the insert 190 may be centered between the exterior surface 104 and the interior surface 130. In some embodiments, the insert 190 may be closer to the exterior surface 104 than the interior surface 130. In some embodiments, the insert 190 may be closer to the interior surface 130 than the exterior surface 104. In some embodiments, the insert 190 may be flush with the interior surface 130 or the exterior surface 104. Although illustrated embedded in the body 102 in FIG. 2, in some embodiments, the insert 190 can be attached (by adhesive or mechanical means) to the exterior surface 104 or interior surface 130. The insert 190 can have a thickness $T_2$ as shown. In some embodiments, the thickness $T_2$ can be about 5 mm, 4 mm, 3 mm, 2 mm, 1 mm, or 0.5 mm. Other thicknesses are possible. In some embodiments, the insert 190 is as thick as the body 102. In some embodiments, the insert 190 is about 90%, about 80%, about 70%, about 60%, about 50%, about 40%, about 30%, about 20%, or about 10% as thick as the body 102 (as well as ranges and values between the listed percentages).

Figure 3:
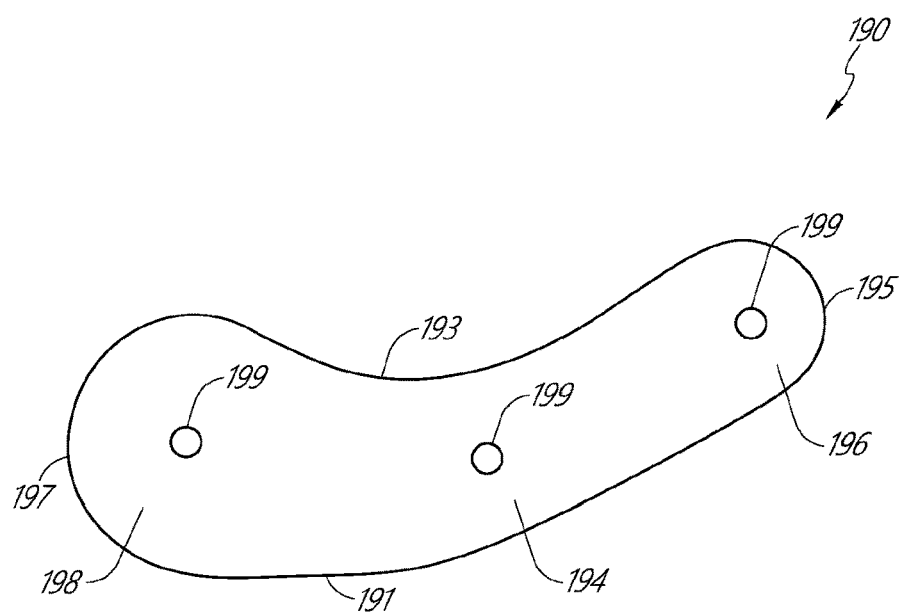
FIG. 3 is a plan view of an insert of the CMC thumb brace of FIG. 1.

FIG. 3 is a plan view of the insert 190. In the illustrated embodiment, the insert 190 includes a CMC portion 194, a dorsal portion 196, and a palmar portion 198. When the brace 100 is worn, the CMC portion 194 can be positioned over the CMC joint, the dorsal portion 196 can wrap around a portion of the dorsum of the hand, and the palmar portion can wrap around a portion of the palm of the hand. The dorsal portion 196 and the palmar portion 198 can each be formed as lobes. In some embodiments, the lobe of the palmar portion 198 is larger than the dorsal portion 196, as illustrated. In some embodiments, the lobe of the dorsal portion 196 can be larger than the lob of the palmar portion 198. In some embodiments, the lobes of the dorsal portion 196 and the palmar portion 198 can be approximately the same size.

The insert 190 includes a proximal edge 191 and an opposite distal edge 193. On the dorsal end the proximal edge 191 is connected to the distal edge 193 by a dorsal edge 195. On the palmar end the proximal edge 191 is connected to the distal edge 193 by a palmar edge 197. In some embodiments, the dorsal edge 195 comprises a curve having a substantially constant radius. In some embodiments, the palmar edge 197 comprises a curve having a substantially constant radius. In some embodiments, the proximal edge 191 includes a convex curve. In some embodiments, the distal edge 193 includes a concave curve. Thus, in some embodiments, the insert 190 comprises a general C-shape. In some embodiments, one end of the C-shape curves towards the first and second palmar straps 108, 110, and the opposite end of the C-shape curves towards the dorsal projection 112. Other shapes for the insert 190 are possible.

The insert 190 can be positioned within the body 102 within the wrist strap 106, and/or the proximal portions 132, 156, 180 of the first and second palmar straps 108, 110 and the dorsal projection 112. In general, when worn, the insert 190 can be positioned over or below the CMC joint and curves around the patient's wrist or the base of the patient's thumb.

In the illustrated embodiment, the insert 190 includes holes 199 formed therethrough. Three holes 199 are illustrated, although other numbers and locations are possible. The holes 199 may be used to position the insert 190 in the mold (see FIG. 11) so that the elastomeric material of the body 102 can be poured around the insert 190.

As mentioned above, in some embodiments, the insert 190 is made a polymer that is heat moldable. The heat-moldable polymer can have, for example, a medium to high flexural modulus and/or a medium to high elongation or tensile strength. In some embodiments, the heat-moldable polymer is heat moldable at temperatures between about 130° F., about 150° F., or about 165° F. and about 250° F. or about 275° F. but stiff at temperatures below about 130° F., about 150° F., or about 165° F. The insert 190 can thus be moldable to fit a particular patient's anatomy. In certain implementations, the insert 190 is heat formable so that it can be fit in real time to the patient, then stiffen as it cools for patient-specific fit. Examples of suitable materials for the insert 190 include thermoplastic alloys formed from one or more polymers. Suitable polymers include polyester, polyetheylene, polyvinyl chloride, polyethylene tetraphthalate, polyamide, or PVC foam such as Sintra™ or Komatex™, or combinations thereof. An example of a suitable heat-moldable material for the insert 190 includes a thermoformable material provided by DJO Global under the trademark "Exos 40BX."

When the brace 100 includes a heat-moldable insert 190 it can be formed and custom shaped to a patient's anatomy by heating the brace 100 at a relatively low temperature (such that the heat-moldable insert 190 becomes pliable), placing the heated brace 100 on the patient, and applying pressure to custom form the brace 100 to the patient as the brace 100 cools and the insert 190 hardens. An example process for conforming or molding the brace 100 to the specific and unique musculoskeletal shape of a patient will now be described in detail.

As an initial step, a brace 100 having a general shape is provided. The general shape may be the flat shape illustrated in FIG. 1, for example. The general shape may be preconfigured to fit generally around the patient wrist and thumb. In some embodiments, the general shape is configured as a one-size-fits-all shape that can be molded, according the method described herein to fit a particular patient. In some embodiments, a patient or a healthcare provider may select a brace 100 having a general shape from among a limited number of size options. For example, in some embodiments, braces 100 may be provided in a first size with a general shape configured to fit adults and a second size with a general shape configured to fit children.

Next, the brace 100 can be heated in a heating/warming source to the prescribed temperature, which in some embodiments is between about 130° F., about 150° F., or about 165° F. and about 250° F. or about 275° F. As the brace 100 is heated, the insert 190 becomes pliable and moldable. The elastomeric body 102 is not substantially affected by heating, and in some embodiments, can be heated with the insert 190. Once the desired temperature is achieved, brace 100 can be removed from the heating/warming source. In some embodiments, the heating/warming device may be portable. This may allow a healthcare provider to bring the heating/warming device to the patient. This may be advantageous because it may allow for a complete custom fitting in a single home visit. In some embodiments, however, the brace 100 can be heated in any conventional heating source capable of heating to the prescribed temperature, including a conventional home oven. This may allow a user to purchase a brace 100 and then custom fit it at home. In some embodiments, however, it is advantageous to have a healthcare provider custom fit the brace 100 a proper fitting.

Next, the heated brace 100 can be placed on the wrist (for example, as shown in FIGS. 6-8). A medical professional may hold the wrist and thumb in a desired alignment. The medical professional can then gently mold the insert 190 to the specific shape of the patient's wrist and thumb by applying gentle pressure. In some embodiments, the medical professional may apply pressure to the brace 100 with his/her hands in order to mold the insert 190 to the specific shape of the patient. In some embodiments, the various closures systems connecting the palmar straps 108, 110 to the dorsal projection 112 (described above) may be tightened while the brace 100 remains heated and the pressure of the closure may mold the insert 190 to the contours of a patient.

As the brace 100 cools, the insert 190 hardens in the molded configuration about the wrist and thumb, providing a stabilizing brace structure that is specific to the patient. In some embodiments, the brace 100 can be re-heated and re-shaped to adjust the configuration of the brace 100 in response to changes in the patient's anatomy such as swelling.

Figure 13:
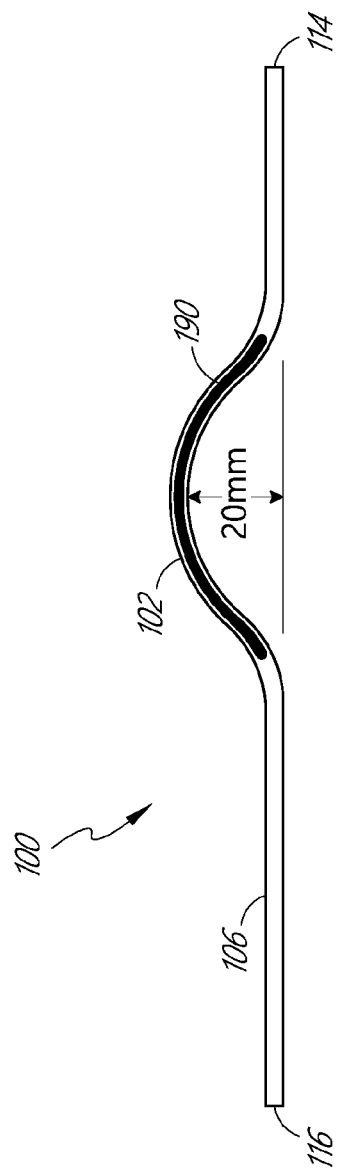
FIG. 13 is an end view of CMC thumb brace of FIG. 12, illustrated when not worn by a patient and lying flat and after the brace has been heat molded to conform to a wearer's anatomy.

As shown in FIG. 13, for example, in some embodiments, after the insert 190 has been heat molded, it may retain a curved shape. In some embodiments, the insert 190 may be manufactured to include the curved shape shown in FIG. 13.

FIGS. 6-8 illustrate an example of the brace 100 as worn by a patient. FIG. 6 is a dorsal view of a right hand wearing the brace 100. FIG. 7 is palmar view of the right hand wearing the brace 100. FIG. 8 is a perspective view of a right hand wearing the brace 100. As shown in these FIGS. 6-8, in some embodiments, when the brace 100 is worn, the insert 190 is positioned over the CMC joint of the thumb and wraps around the patient's wrist and thumb. This can provide support and bracing for CMC joint.

As shown, the wrist strap 106 can encircle the patient's wrist and can be connected by the connector or fastener 200. The first and second palmar straps 108, 110 can extend across a portion of the palm, over the purlicue, and connect to the dorsal projection 112 by connectors 200. In some embodiments, one or both of the first and second palmar straps 108, 110 extend over a portion of the thenar eminence of the palm.

Various other features of the brace 100 are also illustrated in FIGS. 6-7 and correspond with similarly numbered features described above with reference to FIG. 1.

Figure 9:
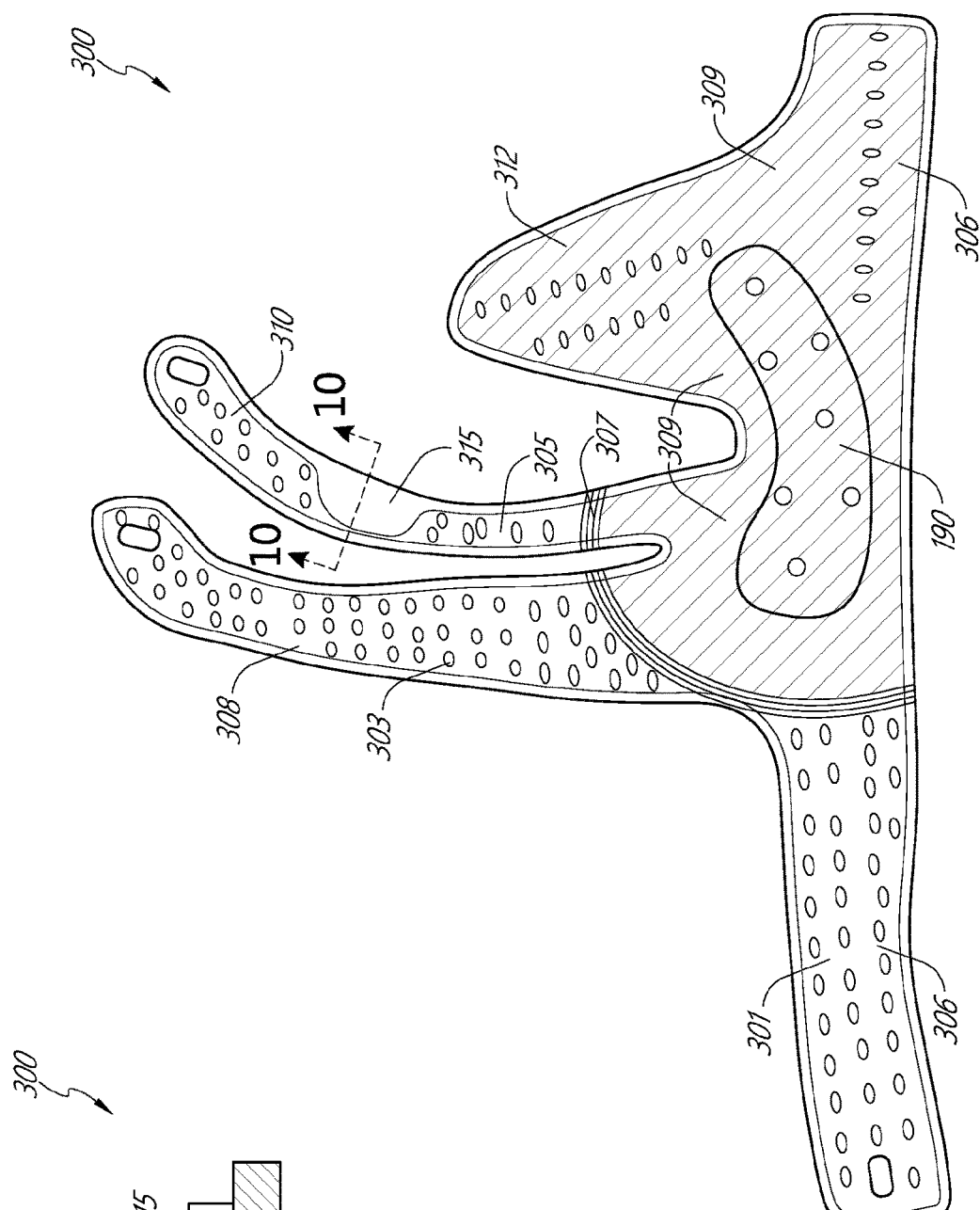
FIG. 9 is a plan view of an exterior side of another embodiment a CMC thumb brace, illustrated when not worn by a patient and lying flat.

FIG. 9 is a plan view of an exterior side of another embodiment a CMC thumb brace 300 (the "brace 300), illustrated when not worn by a patient and lying flat. In many aspects, the brace 300 is similar to the brace 100 described above. For example, the brace 300 includes a wrist strap 306, a first palmar strap 308, a second palmar strap 310, and a dorsal projection 312 that are similar to corresponding features described above. The brace 300 can also include an insert 190 as described above.

Figure 10:
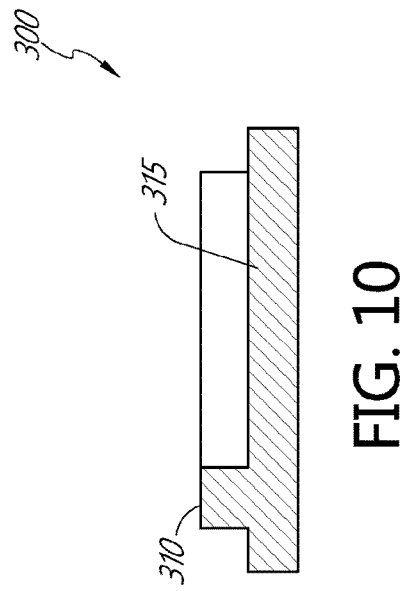
FIG. 10 is a cross-sectional view of a strap of the CMC thumb brace taken along the line illustrated in FIG. 9.

As illustrated in FIG. 9, the second dorsal strap 310 of the brace 300 includes a thinner portion 315. FIG. 10 is a cross-sectional view of the second dorsal strap 310 of the brace 300 taken along the line illustrated in FIG. 9 and illustrates the thinner portion 315. The thinner portion 315 may be positioned on the second dorsal strap 310 at a location that overlies the purlicue when the brace is worn. The thinner portion 315 can facilitate wrapping the second dorsal strap 310 over the purlicue. Although not illustrated, the first dorsal strap 308 can also include a similar thinner portion.

FIG. 9 also illustrates that a variety of surface textures 301, 303, 305, 307, 309 can be applied to the exterior surface of the brace 300. In the illustrated embodiment, a first surface texture 301, formed as a pattern of slightly indented circles is formed over a portion of the wrist strap 306. A second surface texture 303, also formed as a pattern of slightly indented circles, is formed over a portion of the first palmar strap 308. A third surface texture 305, formed as pattern of slightly indented hexagons, can be formed over a portion of the second palmar strap 310. A fourth surface texture 307, formed as a radial pattern of slightly indented grooves, divides the first surface texture 301, the second surface texture 303, and the third surface texture 305, from a fifth surface texture 309. The fifth surface texture 309 is formed as pattern of diagonal indented grooves over another portion of the wrist strap 306, the dorsal projection 312, and portions of the first and second palmar straps 308, 310. Other surface textures and locations are possible. In some embodiments, the surface textures are omitted. In some embodiments, the textures can enhance grip and/or breathability.

FIG. 11 illustrates an embodiment of mold 400 that can be used to manufacture a CMC brace as described above. In the illustrated embodiment, the mold 400 includes a depression or recess 402 that corresponds in size and shape to the body 102 of the brace 100. The mold includes one or more protrusions 406 that extend upwardly from the recess 402. The protrusions 406 are configured in size, shape, and position to form the various apertures (e.g., apertures 126, 128, 148, 150, 152, 172) of the brace 100. The mold 400 can also include posts 408. The posts 408 are configured to support the insert 190 within the mold. For example, as shown, the insert 190 can be placed on the posts 408. An additional protrusion 410 can be included to form a logo into the molded brace. The mold 400 can also include various surface textures 412, 414, 416 so as to form various surface textures on the brace (see, e.g., the brace 300 of FIG. 9).

A method of manufacturing the brace 100 can include, for example, providing the mold 400; positioning an insert 190 onto the posts 408; and pouring a liquid material into the mold. The liquid material can comprise, for example, an elastomeric material, such as silicone, as described above. The liquid material can fill the recess 402 of the mold 400. The liquid material can, in some embodiments, flow below and above the insert 190 such that the insert 190 becomes embedded in the material. The method can also include allowing the material to solidify and removing the formed brace from the mold 400. Other methods of manufacture are also possible.

Figure 12:
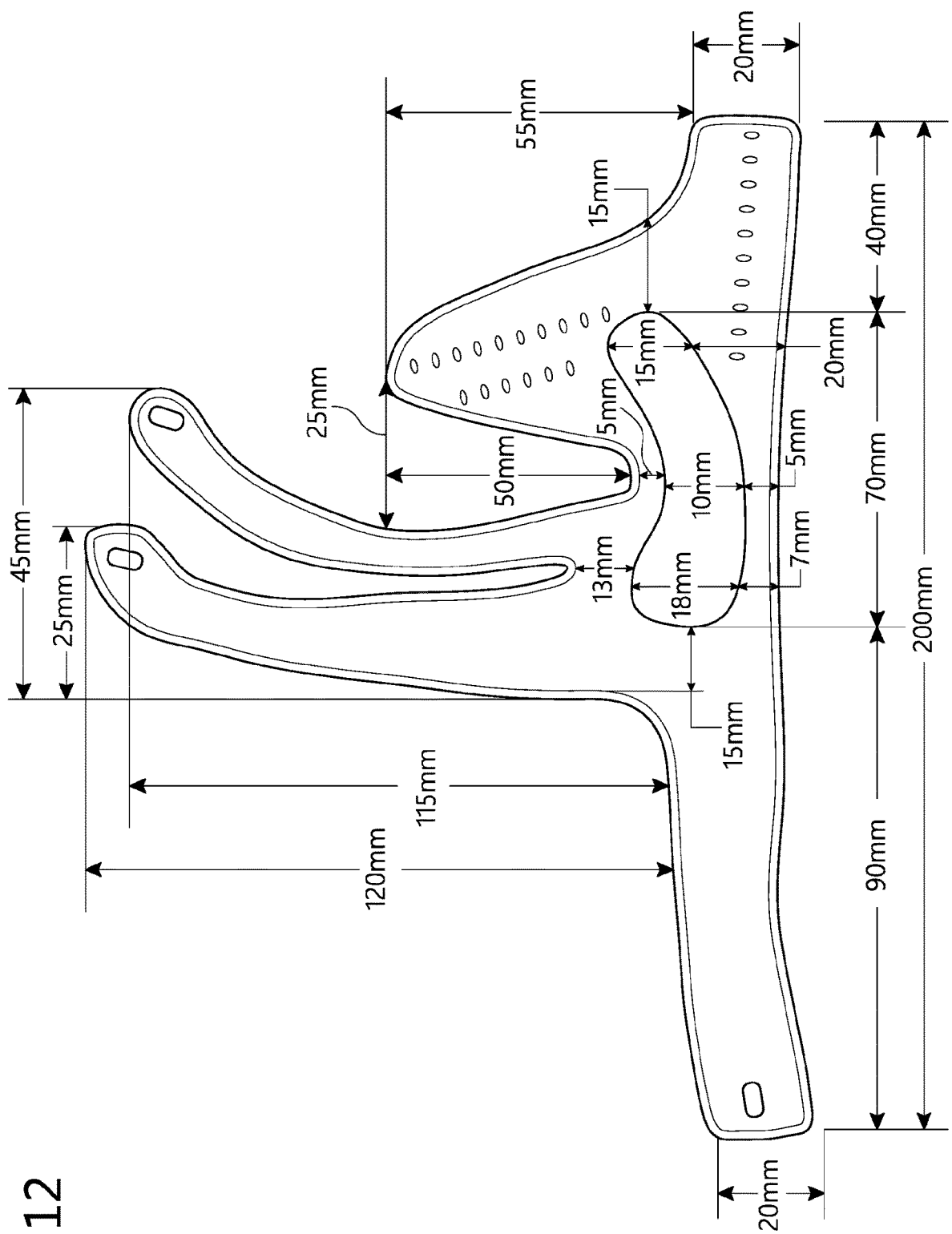
FIG. 12 is a plan view of an exterior side of another embodiment a CMC thumb brace, illustrated when not worn by a patient and lying flat, illustrating several example dimensions of the CMC thumb brace.

FIGS. 12 and 13 illustrate example dimensions for one embodiment of a CMC thumb brace. The illustrated embodiment and dimensions are provided by way of one example only and are not intended to be limiting. FIG. 13 illustrates a side view of the CMC thumb brace that includes an insert 190 that has been heat molded to conform to a patient. The illustrated dimension is a height of a curve formed in the brace measured when the brace is lying flat. Again, the illustrated dimensions are only examples, and other dimensions can be used in other embodiments.

In some embodiments, the braces described herein can be used post operation after basilar joint reconstruction surgery.

The foregoing description details certain embodiments of the systems, devices, and methods disclosed herein. It will be appreciated, however, that no matter how detailed the foregoing appears in text, the systems, devices, and methods can be practiced in many ways. As is also stated above, it should be noted that the use of particular terminology when describing certain features or aspects of the invention should not be taken to imply that the terminology is being redefined herein to be restricted to including any specific characteristics of the features or aspects of the technology with which that terminology is associated.

It will be appreciated by those skilled in the art that various modifications and changes may be made without departing from the scope of the described technology. Such modifications and changes are intended to fall within the scope of the embodiments. It will also be appreciated by those of skill in the art that parts included in one embodiment are interchangeable with other embodiments; one or more parts from a depicted embodiment can be included with other depicted embodiments in any combination. For example, any of the various components described herein and/or depicted in the figures may be combined, interchanged or excluded from other embodiments.

The above description discloses several methods and materials of the present invention. This invention is susceptible to modifications in the methods and materials, as well as alterations in the fabrication methods and equipment. Such modifications will become apparent to those skilled in the art from a consideration of this disclosure or practice of the invention disclosed herein. Consequently, it is not intended that this invention be limited to the specific embodiments disclosed herein, but that it cover all modifications and alternatives coming within the true scope and spirit of the invention as embodied in the attached claims. Applicant reserves the right to submit claims directed to combinations and sub-combinations of the disclosed inventions that are believed to be novel and non-obvious. Inventions embodied in other combinations and sub-combinations of features, functions, elements and/or properties may be claimed through amendment of those claims or presentation of new claims in the present application or in a related application. Such amended or new claims, whether they are directed to the same invention or a different invention and whether they are different, broader, narrower or equal in scope to the original claims, are to be considered within the subject matter of the inventions described herein.

What is claimed is:

1. A brace for a carpometacarpal joint of a thumb, comprising:
a body made of an elastomeric material, the body including
a wrist strap configured to surround a wrist,
a dorsal projection extending from the wrist strap, the dorsal projection configured to extend across a portion of a dorsum of a hand,
a first palmar strap extending between a proximal end connected to the wrist strap and a distal end, the first palmar strap configured to extend across a portion of a palm of the hand and over a purlicue of the hand, the distal end configured to removably attach to the dorsal projection, and
a second palmar strap extending between a proximal end connected to the wrist strap and a distal end, the second palmar strap configured to extend across a portion of the palm of the hand and over the purlicue of the hand, the distal end configured to removably attach to the dorsal projection; and
an insert positioned within the body, the insert comprising a heat-moldable material that is pliable above a temperature and substantially stiff below the temperature, the insert positioned within the body so as to be positioned over a carpometacarpal joint of a thumb.

2. The brace of claim 1, wherein the elastomeric material comprises silicone.

3. The brace of claim 1, wherein the elastomeric material comprises a thermoplastic elastomer.

4. The brace of claim 1, wherein the temperature is between approximately 130° F. and approximately 250° F.

5. The brace of claim 1, wherein the second palmar strap is connected to the wrist strap between a connection of the first palmar strap to the wrist strap and the dorsal projection.

6. The brace of claim 5, wherein the first palmar strap and the second palmar strap extend from the wrist strap to a length that is longer that a length that the dorsal projection extends from the wrist strap.

7. The brace of claim 6, wherein a distal end of the first palmar strap extends from the wrist strap farther than a distal end of the second palmer palmar strap extends from the wrist strap.

8. The brace of claim 5, wherein the first palmar strap is separated from the second palmar strap by a gap that is smaller than a gap separating the second palmar strap and the dorsal projection.

9. A brace for a carpometacarpal joint of a thumb of a hand, comprising:
a body including
a wrist strap;
a dorsal projection extending from the wrist strap;
a first palmar strap extending between a proximal end connected to the wrist strap and a distal end, the first palmar strap configured to extend across a portion of a palm of the hand and over a purlicue of the hand, the distal end configured to removably attach to the dorsal projection, and
a second palmar strap extending between a proximal end connected to the wrist strap and a distal end, the second palmar strap configured to extend across a portion of the palm of the hand and over the purlicue of the hand, the distal end configured to removably attach to the dorsal projection.

10. The brace of claim 9, wherein the body comprises an elastomeric material.

11. The brace of claim 10, wherein the elastomeric material comprises silicone.

12. The brace of claim 10, wherein the elastomeric material comprises a thermoplastic elastomer.

13. The brace of claim 9, further comprising an insert embedded within the body so as to be positioned over a CMC joint of the thumb when the brace is worn.

14. The brace of claim 13, wherein the insert comprises a stiff material.

15. The brace of claim 13, wherein the insert comprises a heat-moldable material that is pliable above a temperature and stiff below the temperature.

16. The brace of claim 15, wherein the temperature is between approximately 130° F. and approximately 250° F.

17. The brace of any of claim 9, wherein the wrist strap is configured in size and shape to encircle a patient's wrist when the brace is worn.

18. The brace of any of claim 9, wherein the first and second palmar straps are each configured in size and shape to extend across a portion of the palm of the hand and over the purlicue of the hand.

19. The brace of any of claim 9, wherein the dorsal projection is configured in size and shape to extend across a portion of a dorsum of the hand.

20. A brace for a carpometacarpal joint of a thumb, comprising:
 a body including
  a wrist strap configured to encircle a patient's wrist when the brace is worn, and
  a first palmar strap connected on a first end to a first location of the wrist strap and connected on a second end to a second location of the wrist strap, the strap configured in size and shape to extend across a portion of the patient's palm, over a purlicue, and across a portion of a dorsum of the patient's hand, and
  a second palmar strap connected on a first end to a first location of the wrist strap and connected on a second end to a second location of the wrist strap, the strap configured in size and shape to extend across a portion of the patient's palm, over the purlicue, and across a portion of the dorsum of the patient's hand; and
 an insert embedded within the body, the insert comprising a heat-moldable material that is pliable above a temperature and stiff below the temperature.

* * * * *